United States Patent
Jiao et al.

(10) Patent No.: US 11,827,945 B2
(45) Date of Patent: Nov. 28, 2023

(54) MULTIPLEX PCR DETECTION KIT FOR LISTERIA MONOCYTOGENES SEROTYPE 4H

(71) Applicant: Yangzhou University, Yangzhou (CN)

(72) Inventors: Xin'an Jiao, Yangzhou (CN); Yuelan Yin, Yangzhou (CN); Youwei Feng, Yangzhou (CN); Hao Yao, Yangzhou (CN); Xinyu Sun, Yangzhou (CN); Zhiming Pan, Yangzhou (CN); Xiang Chen, Yangzhou (CN); Jing Wang, Yangzhou (CN)

(73) Assignee: Yangzhou University, Yangzhou (CN)

( * ) Notice: Subject to any disclaimer, the term of this patent is extended or adjusted under 35 U.S.C. 154(b) by 0 days.

(21) Appl. No.: 17/617,942

(22) PCT Filed: May 27, 2020

(86) PCT No.: PCT/CN2020/092600
§ 371 (c)(1),
(2) Date: Dec. 10, 2021

(87) PCT Pub. No.: WO2020/248819
PCT Pub. Date: Dec. 17, 2020

(65) Prior Publication Data
US 2022/0307074 A1    Sep. 29, 2022

(30) Foreign Application Priority Data
Jun. 11, 2019 (CN) .......................... 201910502008.0

(51) Int. Cl.
C12Q 1/68 (2018.01)
C12Q 1/689 (2018.01)
C12Q 1/686 (2018.01)

(52) U.S. Cl.
CPC ............. *C12Q 1/689* (2013.01); *C12Q 1/686* (2013.01); *C12Q 2600/16* (2013.01)

(58) Field of Classification Search
CPC ............................... C12Q 1/686; C12Q 1/689
See application file for complete search history.

(56) References Cited

U.S. PATENT DOCUMENTS

2019/0056407 A1    2/2019    Tamura et al.

FOREIGN PATENT DOCUMENTS

| CN | 107746890 A | 3/2018 |
|---|---|---|
| CN | 109735638 A | 5/2019 |
| CN | 110218805 | 9/2019 |
| WO | 2017009198 A | 1/2017 |

OTHER PUBLICATIONS

Chatterjee et al., 2006. Invasiveness is a variable and heterogeneous phenotype in Listeria monocytogenes serotype strains. International journal of medical microbiology, 296(4-5), pp. 277-286. (Year: 2006).*
Chen et al., 2017. PCR-based methodologies for detection and characterization of Listeria monocytogenes and Listeria ivanovii in foods and environmental sources. Food Science and Human Wellness, 6(2), pp. 39-59. (Year: 2017).*
Doumith et al., 2004. Differentiation of the major Listeria monocytogenes serovars by multiplex PCR. Journal of clinical microbiology, 42(8), pp. 3819-3822. (Year: 2004).*
Feng et al., 2020. Rapid detection of hypervirulent serovar 4h Listeria monocytogenes by multiplex PCR. Frontiers in microbiology, 11, 1309, pp. 1-7. (Year: 2020).*
Genbank Accession No. CP007195—Listeria monocytogenes serotype 1/2c str. 10-5026, complete genome (submitted by Feb. 5, 2014, retrieved on Sep. 10, 2022 from http://www.ncbi.nlm.nih.gov/nuccore/CP007195). (Year: 2014).*
Genbank Accession No. CP007583—Listeria monocytogenes strain XYSN, complete genome, submitted by Apr. 3, 2014, retrieved on Sep. 10, 2022 from http://www.ncbi.nlm.nih.gov/nuccore/CP007583). (Year: 2014).*
Kuenne et al., 2013. Reassessment of the Listeria monocytogenespan-genome reveals dynamic integration hotspots and mobile genetic elements as major components of the accessory genome. BMC genomics, 14(1), pp. 1-19. (Year: 2013).*
Liu et al., 2007. A multiplex PCR for species-and virulence-specific determination of Listeria monocytogenes. Journal of Microbiological Methods, 71(2), pp. 133-140. (Year: 2007).*
Yin et al., 2019. A hybrid sub-lineage of Listeria monocytogenes comprising hypervirulent isolates. Nature communications, 10(1), pp. 1-16. (Year: 2019).*
S.W. Nho et al., "Identification of high-risk Listeria monocytogenes serotypes in lineage I (serotype 1/2a, 1/2c, 3a and 3c) using multiplex PCR", «Journal of Applied Microbiology» , date:Sep. 30, 2015, 119-3, pp. 845-852 see the whole document, publisher: Blackwell Publishing Inc., England.

* cited by examiner

*Primary Examiner* — Teresa E Strzelecka
*Assistant Examiner* — Olayinka A Oyeyemi

(57) ABSTRACT

The present invention provides a multiplex PCR detection kit of *Listeria monocytogenes* serotype 4h. The kit includes a gene lmo1210 detection primer and a gene xysn_1693 detection primer. The present invention establishes a multiplex PCR method for rapidly detecting *Listeria monocytogenes* serotype 4h by using two pairs of primers.

3 Claims, 2 Drawing Sheets

Specification includes a Sequence Listing.

SEQUENCE LISTING

<160> NUMBER OF SEQ ID NOS: 8

<210> SEQ ID NO 1
<211> LENGTH: 468
<212> TYPE: DNA
<213> ORGANISM: Artificial Sequence
<220> FEATURE:
<223> OTHER INFORMATION: lmo1210 nucleotide sequence

<400> SEQUENCE: 1

```
atgacaaaaa gatcatccaa atcattatta ctatttatgg caatgggact tgtttctgga      60
ctactttccc cgattcaaac gtcgattaat agccaacttc ggctaactgt cggttctcct     120
tttgtggcat catttatttc cttttagtt gggacgactt tgcttacact ggtttgttta     180
atcgttgagc gtcgtttgac ttttcaactg aaaggtgtcg gccgaattcc ttggtgggtt     240
ttcactggcg gtgcgcttgg agtgctcttc gtaacttcta acattttact tttaccatta     300
ctcggctcag caatgacggt tgttttagcg ctttgtgggc aaatgattat tgcacttatt     360
```

```
attgatcatt ttggttttt cggggttatt cctcatccaa ttaaccgtta tcgtatgatt      420
ggtgttttat taatgcttat tggtgtattt ttaattcaac gtttttaa                  468

<210> SEQ ID NO 2
<211> LENGTH: 534
<212> TYPE: DNA
<213> ORGANISM: Artificial Sequence
<220> FEATURE:
<223> OTHER INFORMATION: xysn_1693 nucleotide sequence

<400> SEQUENCE: 2
atgaagaaag acataaaaaa gagatacatt agtttaatag taattggggc attgatggtg      60
ggtatgacct ttccttatgg tactaccgta catgcagaca gtgttcaaag tgataactta     120
tatccaagtg atcaagtgaa tactgataat cagtttattg tcttggatga ttacactata     180
acggatgagg aaggtaatat agttaatgag gagcagaata aaaattcaca tcttcttaag     240
tcagctacag ggttccacta caaaacattg tctcagtcaa tgaaaaaggg tagcagaact     300
tatttgggaa aaagaaata  taaaaaaggc tttgattta  gtgtgaaagt aatcgtaaaa     360
ggtgtatatg ttaacttggg aggatatgca tcaaaaactg gatattataa agagtataaa     420
caaaatgtaa agataactgt taaagttaaa aaatatgaaa atggatcagg aaagtatgtt     480
ggaacctaca cctatacatc taatacttca tatgtagata gaattccagt ataa           534

<210> SEQ ID NO 3
<211> LENGTH: 21
<212> TYPE: DNA
<213> ORGANISM: Artificial Sequence
<220> FEATURE:
<223> OTHER INFORMATION: 1mol210F

<400> SEQUENCE: 3
gtcgtttgac ttttcaactg a                                                21

<210> SEQ ID NO 4
<211> LENGTH: 21
<212> TYPE: DNA
<213> ORGANISM: Artificial Sequence
<220> FEATURE:
<223> OTHER INFORMATION: 1mol210R

<400> SEQUENCE: 4
attggatgag gaataacccc g                                                21

<210> SEQ ID NO 5
<211> LENGTH: 211
<212> TYPE: DNA
<213> ORGANISM: Artificial Sequence
<220> FEATURE:
<223> OTHER INFORMATION: nucleotide sequence of the amplification region
      of the forward and reverse primers for 1mol210

<400> SEQUENCE: 5
gtcgtttgac ttttcaactg aaaggtgtcg gccgaattcc ttggtgggtt ttcactggcg      60
gtgcgcttgg agtgctcttc gtaacttcta acatttact  tttaccatta ctcggctcag    120
caatgacggt tgttttagcg ctttgtgggc aaatgattat tgcacttatt attgatcatt    180 ttggttttt cggggttatt cctcatccaa t                                     211

<210> SEQ ID NO 6
<211> LENGTH: 22
```

```
<212> TYPE: DNA
<213> ORGANISM: Artificial Sequence
<220> FEATURE:
<223> OTHER INFORMATION: xysn_1693F

<400> SEQUENCE: 6
tccaacatac tttcctgatc ca                                              22

<210> SEQ ID NO 7
<211> LENGTH: 22
<212> TYPE: DNA
<213> ORGANISM: Artificial Sequence
<220> FEATURE:
<223> OTHER INFORMATION: xysn_1693R

<400> SEQUENCE: 7
atggtgggta tgacctttcc tt                                              22

<210> SEQ ID NO 8
<211> LENGTH: 429
<212> TYPE: DNA
<213> ORGANISM: Artificial Sequence
<220> FEATURE:
<223> OTHER INFORMATION: nucleotide sequence of the amplification region
      of the forward and reverse primers for xysn_1693

<400> SEQUENCE: 8
tccaacatac tttcctgatc cattttcata tttttttaact ttaacagtta tctttacatt    60
ttgtttatac tctttataat atccagtttt tgatgcatat cctcccaagt taacatatac   120
accttttacg attactttca cactaaaatc aaagcctttt ttatatttct tttttcccaa   180
ataagttctg ctaccttttt tcattgactg agacaatgtt ttgtagtgga acctgtagc    240 tgacttaaga agatgtgaat ttttattctg ctcctcatta actatattac cttcctcatc   300
cgttatagtg taatcatcca agacaataaa ctgattatca gtattcactt gatcacttgg   360
atataagtta tcactttgaa cactgtctgc atgtacggta gtaccataag gaaaggtcat   420
acccaccat                                                           429
```

MULTIPLEX PCR DETECTION KIT FOR LISTERIA MONOCYTOGENES SEROTYPE 4H

TECHNICAL FIELD

The present invention relates to a biological detection kit, and in particular, to a multiplex PCR detection kit of *Listeria monocytogenes* serotype 4h.

BACKGROUND

*Listeria monocytogenes* (LM) is an important food-borne zoonotic pathogen, and the harm to food safety and human health has attracted much attention from many countries. Listeriosis caused by *Listeria monocytogenes* in human and animal has the characteristics of low morbidity and high lethality. According to statistics, the morbidity of human Listeriosis is about 0.1-11.3 per million people, and the mortality is 20%-30%.

*Listeria monocytogenes* includes 4 evolutionary lineages and 14 serotypes. Among them, 1/2a, 1/2b and 4b are main serotypes causing listeriosis, and 4h is a novel serotype of *Listeria* discovered in China. Serotype 4h of *Listeria monocytogenes* usually has a hyper-virulent property, and the outbreak of listeriosis is mostly related to the occurrence of hyper-virulent strains, so that the establishment of a rapid and effective method for detecting *Listeria monocytogenes*, especially serotype 4h, is very necessary for the monitoring and control of the *Listeria*.

Methods for detecting *Listeria monocytogenes* in food generally refer to the National Food Safety Standard GB 4789.30-2016, and a conventional biochemical identification experiment is carried out after the enrichment culture and the selective culture of the sample. This method can detect the *Listeria monocytogenes* more accurately, but has the defects of much time and labor consumption and cannot quickly distinguish the hyper-virulent *Listeria monocytogenes*.

Therefore, it is necessary to provide a new rapid and convenient detection method.

SUMMARY

The present invention provides a multiplex PCR detection kit of *Listeria monocytogenes* serotype 4h, which is used for directly detecting *Listeria monocytogenes* serotype 4h. The method is simple in operation, high in accuracy, and short in time consumption, and meets the needs of current food safety testing.

A first aspect of the present invention provides a use of gene lmo1210 and gene xysn_1693 in the preparation of a detection kit for detecting *Listeria monocytogenes* serotype 4h.

The use of the gene lmo1210 and the gene xysn_1693 in the preparation of detection kit for *Listeria monocytogenes* serotype 4h means that the gene lmo1210 and the gene xysn_1693 are used as detection targets for detecting *Listeria monocytogenes* serotype 4 h.

In some embodiments of the present invention, based on the sequences of the gene lmo1210 and the gene xysn_1693, an amplification primer pair specific for the gene lmo1210 and the gene xysn_1693 is screened as a detection reagent for *Listeria monocytogenes* serotype 4h.

The abovementioned use should be the result of the co-action of the gene lmo1210 and the gene xysn_1693, rather than the result of the action of individual genes.

The present invention provides a multiplex PCR detection kit of *Listeria monocytogenes* serotype 4h, which includes a gene lmo1210 detection primer and a gene xysn_1693 detection primer.

Preferably, the gene lmo1210 detection primer includes a forward primer with a nucleotide sequence shown in SEQ ID NO. 3 and a reverse primer with a nucleotide sequence shown in SEQ ID NO. 4.

Further, the amplification region of the gene lmo1210 detection primer has a nucleotide sequence shown in SEQ ID NO: 5. The detection fragment is 211 bp in length.

Preferably, the gene xysn_1693 detection primer includes a forward primer with a nucleotide sequence shown in SEQ ID NO. 6 and a reverse primer with a nucleotide sequence shown in SEQ ID NO. 7.

Further, the amplification region of the gene xysn_1693 detection primer has a nucleotide sequence shown in SEQ ID NO: 8. The detection fragment is 429 bp in length.

The present invention detects the gene lmo1210 and the gene xysn_1693 using PCR technology, and can determine whether the detected subject belongs to the *Listeria monocytogenes* serotype 4h according to the amplification condition. Therefore, the design of the primer is the key of the kit of the present invention.

The detection is carried out by the kit according to the present invention using PCR technology, so the kit may further include other reagents required for PCR, for example, one or more of PCR reaction reagents such as ddH2O, dNTP, PCR buffer, rTaq enzyme and sample genomic DNA extraction reagent. Since such PCR reagents can be purchased separately from the market or formulated by oneself, the specific reagents that need to be assembled into the kit can be determined according to the actual needs of the customer, or all reagents can be assembled into the kit for convenience.

The kit of the present invention may contain a primer pair packaged independently, or may contain a prepared PCR detection solution containing a primer pair.

The PCR detection solution may be formulated by oneself or obtained by directly adding primers into a common PCR reaction solution which is commercially available and does not contain the primers. For example, the kit may further contain ddH2O, dNTP, PCR buffer, and rTaq enzyme. The PCR reaction system can be obtained by adding the primer of the present invention, the DNA extract of the sample to be detected or the sample bacterial liquid.

Preferably, the kit may further contain a positive control. The positive control is a DNA sample containing gene lmo1210 and/or gene xysn_1693.

Preferably, the kit may further include a negative control. The negative control may be a DNA sample without gene lmo1210 and gene xysn_1693.

A second aspect of the present invention provides a detection method by using the above multiplex PCR detection kit, including the steps of:
(1) extracting a sample genomic DNA;
(2) adding samples: respectively adding the sample genomic DNA, a positive control and/or a negative control into PCR tubes provided with a PCR reaction system to correspondingly obtain a sample reaction tube, a positive reaction tube and/or a negative reaction tube, where the PCR reaction system includes the above gene lmo1210 and gene xysn_1693 detection primers;
(3) PCR reaction: placing the reaction tubes on a PCR instrument, and setting circulation parameters, to carry out a PCR reaction; and (4) analyzing results after the PCR reaction is completed.

The above method is a method for non-disease diagnosis purposes.

Further, in step (1), extracting a sample genomic DNA can be prepared by those skilled in the art according to the existing operation method.

Further, the PCR reaction condition in step (3) is: pre-denaturation at 95° C. for 5 min; 35 cycles of denaturation at 95° C. for 30s, annealing at 55° C. for 30s, and extension at 72° C. for 30s; and termination at 72° C. for 10 min.

Further, the result analysis and determination method in step (4) is as follows: if the 211 bp and 429 bp bands are amplified simultaneously, it is determined to be positive for serotype 4h of Listeria monocytogenes; if only the 211 bp band is amplified, it is determined to be positive for other serotypes of Listeria monocytogenes; and if no band is amplified, it is determined to be negative for Listeria monocytogenes.

A third aspect of the present invention provides the use of the above kit in the preparation of gene lmo1210 and gene xysn_1693 detection products.

The detection product is used to detect the Listeria monocytogenes serotype 4h.

As mentioned above, the multiplex PCR detection kit of Listeria monocytogenes serotype 4h of the present invention has the following beneficial effects:

The present invention utilizes PCR amplification technology to establish a multiplex PCR method for rapidly detecting Listeria monocytogenes serotype 4h by using two pairs of primers. This method has the advantages of good specificity, high sensitivity, fast detection, easy with operation and determination of results. Upon testing the actual samples of Listeria and non-Listeria strains, there was no false positive result, which has good specificity.

DETAILED DESCRIPTION OF THE PREFERRED EMBODIMENTS

Figure 1A:
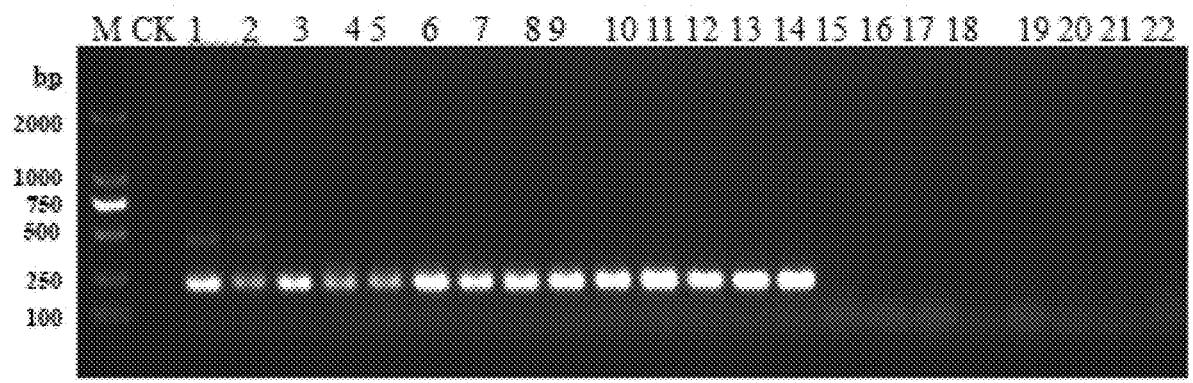
FIG. 1a and FIG. 1b are the experimental results for evaluating specificity of the multiplex PCR method in Embodiment 1 of the present invention. Among them, M: DL2000; CK: Negative control; 1-2: Listeria monocytogenes serotype 4h strain; 3-14: Serotypes 1/2a, 1/2b, 1/2c, 3a, 3b, 3c, 4a, 4ab, 4b, 4c, 4d, and 7 of Listeria monocytogenes, respectively; 15: Listeria ivanovii; 16: Listeria innocua; 17: Listeria seeligeri; 18: Listeria grayi; 19: Listeria welshimeri; 20: Salmonella enteritidis; 21: Salmonella pullorum; 22: Salmonella typhimurium, 23: Vibrio parahaemolyticus; 24: Escherichia coli; 25: Staphylococcus aureus; 26: Campylobacter jejuni; 27: Campylobacter coli.

The following describes embodiments of the present invention by using specific examples. A person skilled in the art may easily understand other advantages and effects of the present invention from the content disclosed in this specification. The present invention may also be implemented or applied through other different specific implementations. Various details in this specification may also be modified or changed based on different viewpoints and applications without departing from the spirit of the present invention.

Before the specific embodiments of the present invention is further described, it should be understood that the protection scope of the present invention is not limited to the following specific implementation, and it should also be understood that the terms used in the examples of the present invention are used to describe the specific implementation, not to limit the protection scope of the present invention. In the specification and claims of the present invention, unless the context clearly indicates otherwise, the singular forms "a", "an", and "the" include plural forms.

When numerical ranges are given in the examples, it should be understood that, unless otherwise specified in the present invention, two endpoints and any value between the two endpoints of each numerical range may be selected. Unless otherwise defined, all technical and scientific terms used in the present invention have the same meaning as commonly understood by a person skilled in the art. In addition to the specific methods, devices, and materials used in the examples, a person skilled in the art may also use any methods, devices, and materials in the related art that are similar or equivalent to the methods, devices, and materials in the examples of the present invention according to the mastery of the related art and the record of the present invention to implement the present invention.

Unless otherwise specified, the experimental methods, detection methods, and preparation methods disclosed in the present invention all adopt conventional molecular biology, biochemistry, chromatin structure and analysis, analytical chemistry, cell culture, and recombinant DNA technology in the technical field and conventional technology in related fields. These technologies have been well explained in the existing literature. For details, see Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, etc.

In the following examples, all primers were synthesized by Nanjing GenScript Biotechnology Co., Ltd.; a bacterial DNA extraction kit was purchased from Tiangen Biotech (Beijing) Co., Ltd.; DNA molecular weight Marker DL2000 and 2×Taq Master mix were purchased from Nanjing Vazyme Biotech Co., Ltd.; and a diagnostic kit for Listeria monocytogenes serotypes was purchased from Denka Seiken.

Embodiment 1: Establishment of a Multiplex PCR Detection Method of *Listeria Monocytogenes* Serotype 4h 1) Primer The whole genome sequence of *Listeria monocytogenes* was downloaded from Genebank for comparison, and two specific target genes Imo1210 and xysn_1693 were finally determined. The primers were analyzed and determined to select the best detection primer pair. The sequences of the two pairs of detection primers and the length of the corresponding amplification products are shown in Table 1.

Imo1210 nucleotide sequence
SEQ ID NO: 1
atgacaaaaagatcatccaaatcattattactatttatggcaatgggact tgtttctggactactttccccgattcaaacgtcgattaatagccaacttc ggctaactgtcggttctccttttgtggcatcatttatttccttttttagtt gggacgactttgcttacactggtttgtttaatcgttgagcgtcgtttgac ttttcaactgaaaggtgtcggccgaattccttggtgggttttcactggcg gtgcgcttggagtgctcttcgtaacttctaacatttttacttttaccatta ctcggctcagcaatgacggttgttttagcgctttgtgggcaaatgattat tgcacttattattgatcattttggttttttcggggttattcctcatccaa ttaaccgttatcgtatgattggtgttttattaatgcttattggtgtattt ttaattcaacgttttaa xysn_1693 nucleotide sequence
SEQ ID NO: 2
atgaagaaagacataaaaaagagatacattagtttaatagtaattgggc attgatggtgggtatgacctttccttatggtactaccgtacatgcagaca gtgttcaaagtgataacttatatccaagtgatcaagtgaatactgataat cagtttattgtcttggatgattacactataacggatgaggaaggtaatat agttaatgaggagcagaataaaaattcacatcttcttaagtcagctacag ggttccactacaaaacattgtctcagtcaatgaaaaaaggtagcagaact tatttgggaaaaagaaatataaaaaaggctttgattttagtgtgaaagt aatcgtaaaaggtgtatatgttaacttgggaggatatgcatcaaaaactg gatattataaagagtataaacaaaatgtaaagataactgttaaagttaaa aaatatgaaaatggatcaggaaagtatgttggaacctacacctatacatc taatacttcatatgtagatagaattccagtataa

TABLE 1

Multiplex PCR detection primers for *Listeria monocytogenes* serotype 4h

| Primer | Sequence | Product length |
|---|---|---|
| Imo1210F | 5'-gtcgtttgacttttcaactga-3' (SEQ ID NO: 3) | 211 bp |
| Imo1210R | 5'-attggatgaggaataacccg-3' (SEQ ID NO: 4) | |

TABLE 1-continued

Multiplex PCR detection primers for *Listeria monocytogenes* serotype 4h

| Primer | Sequence | Product length |
|---|---|---|
| xysn_1693F | 5'-tccaacatactttcctgatcca-3' (SEQ ID NO: 6) | 429 bp |
| xysn_1693R | 5'-atggtgggtatgacctttcctt-3' (SEQ ID NO: 7) | |

2) Preparation of Genomic DNA Template 2 mL of bacterial solution were taken, and the bacterial genomic DNA was prepared according to the conventional bacterial genomic DNA extraction method. Genomic DNA extraction is a common method in the field of molecular biology, and various conventional and commercially available bacterial DNA extraction kits can achieve the extraction of genomic DNA templates.

3) Reaction System and Conditions

The PCR reaction system is: 2×Taq Master mix 12.5 μL; 10 μM primers Imo1210F, Imo1210R, xysn_1693 F and xysn_1693R, each of which is 1 μL; 1 μL of genomic DNA template; ddH2O fills up to 25 μL. PCR amplification reaction condition is: pre-denaturation at 95° C. for 5 min; 35 cycles of denaturation at 95° C. for 30s, annealing at 55° C. for 30s, and extension at 72° C. for 30s; and termination at 72° C. for 10 min; and storage at 4° C.

4) Result Determination

The amplification region of the forward and reverse primers for gene Imo1210 had a nucleotide sequence shown in SEQ ID NO: 5, and the detection fragment was 211 bp in length;

SEQ ID NO: 5:
nucleotide sequence of the amplification region of the forward and reverse primers for Imo1210
gtcgtttgacttttcaactgaaaggtgtcggccgaattccttggtgggtt ttcactggcggtgcgcttggagtgctcttcgtaacttctaacatttttact tttaccattactcggctcagcaatgacggttgttttagcgctttgtgggc aaatgattattgcacttattattgatcattttggttttttcggggttatt cctcatccaat The amplification region of the forward and reverse primers for gene xysn_1693 had a nucleotide sequence shown in SEQ ID NO: 8. The detection fragment is 429 bp in length.
SEQ ID NO: 8:
nucleotide sequence of the amplification region of the forward and reverse primers for xysn_1693
tccaacatactttcctgatccattttcatatttttaacttaacagtta tctttacattttgtttatactctttataatatccagttttttgatgcatat cctcccaagttaacatatacaccttttacgattactttcacactaaaatc aaagccttttttatatttcttttttcccaaataagttctgctacctttt tcattgactgagacaatgttttgtagtggaaccctgtagctgacttaaga agatgtgaattttttattctgctcctcattaactatattccttcctcatc -continued cgttatagtgtaatcatccaagacaataaactgattatcagtattcactt gatcacttggatataagttatcactttgaacactgtctgcatgtacggta gtaccataaggaaaggtcatacccaccat The determination method is as follows: if the 211 bp and 429 bp bands are amplified simultaneously, it is determined to be positive for serotype 4h of *Listeria monocytogenes*; if only the 211 bp band is amplified, it is determined to be positive for other serotypes of *Listeria monocytogenes*; and if no band is amplified, it is determined to be negative for *Listeria monocytogenes*.

5) Experiment for Evaluating Specificity of the Multiplex PCR Method

Table 2 involves a total of 27 bacteria strains. Among them, 19 strains are *Listeria* bacteria, including 2 strains of *Listeria monocytogenes* serotype 4h, 12 strains of other serotypes of *Listeria monocytogenes*, and 1 strain each of *Listeria ivanovii*, *Listeria innocua*, *Listeria seeligeri*, *Listeria grayi*, and *Listeria welshimeri*; 8 strains are non-*Listeria* bacteria, including 1 strain each of *Salmonella enteritidis*, *Salmonella pullorum*, *Salmonella typhimurium*, *Vibrio parahaemolyticus*, *Escherichia coli*, *Staphylococcus aureus*, *Campylobacter jejuni*, and *Campylobacter coli*.

TABLE 2

Reference strains of experiment for evaluating specificity of multiplex PCR detection method of *Listeria monocytogenes* serotype 4h

| Number | Name | Strain number | Serotype |
|---|---|---|---|
| 1 | *Listeria monocytogenes* | XYSN | 4h |
| 2 | *Listeria monocytogenes* | 15LG | 4h |
| 3 | *Listeria monocytogenes* | EGD-e | 1/2a |
| 4 | *Listeria monocytogenes* | LmBJ113 | 1/2b |
| 5 | *Listeria monocytogenes* | LmBJ114 | 1/2c |
| 6 | *Listeria monocytogenes* | LmBJ115 | 3a |
| 7 | *Listeria monocytogenes* | LmBJ116 | 3b |
| 8 | *Listeria monocytogenes* | LmBJ117 | 3c |
| 9 | *Listeria monocytogenes* | LmBJ118 | 4a |
| 10 | *Listeria monocytogenes* | LmBJ119 | 4ab |
| 11 | *Listeria monocytogenes* | NTSN | 4b |
| 12 | *Listeria monocytogenes* | LmBJ122 | 4c |
| 13 | *Listeria monocytogenes* | LmBJ121 | 4d |
| 14 | *Listeria monocytogenes* | LmBJ123 | 7 |
| 15 | *Listeria ivanovii* | YZU0805 | — |
| 16 | *Listeria innocua* | LBJ131 | *Innocua* |
| 17 | *Listeria seeligeri* | LBJ133 | *Seeligeri* |
| 18 | *Listeria grayi* | LBJ136 | *Grayi* |
| 19 | *Listeria welshimeri* | LBJ137 | *Welshimeri* |
| 20 | *Salmonella enteritidis* | C50041 | — |
| 21 | *Salmonella pullorum* | S06004 | — |
| 22 | *Salmonella typhimurium* | W293 | — |
| 23 | *Vibrio parahaemolyticus* | — | — |
| 24 | *Escherichia coli* | — | — |
| 25 | *Staphylococcus aureus* | — | — |
| 26 | *Campylobacter jejuni* | — | — |
| 27 | *Campylobacter coli* | — | — |

The genomic DNA of 27 bacteria strains in Table 2 was used as a template. 12.5 μL of 2×Taq Master mix, 1 μL of genomic DNA template, and 10 μM primers lmo1210F, lmo1210R, xysn_1693 F and xysn_1693R (each of which was 1 μL) were added into the PCR tube, respectively, the mixture was filled up to 25 μL with ddH2O and mixed well, and a negative control was established at the same time. After the multiplex PCR reaction was completed, agarose gel electrophoresis was performed to analyze the results.

Figure 1B:

FIG. 1*a* and FIG. 1*b* are the experimental results for evaluating specificity of the multiplex PCR method. Among them, M: DL2000; CK: Negative control; 1-2: *Listeria monocytogenes* serotype 4h strain; 3-14: Serotypes 1/2a, 1/2b, 1/2c, 3a, 3b, 3c, 4a, 4ab, 4b, 4c, 4d, and 7 of *Listeria monocytogenes*, respectively; 15: *Listeria ivanovii*; 16. *Listeria innocua*; 17: *Listeria seeligeri*; 18: *Listeria grayi*; 19: *Listeria welshimeri*; 20: *Salmonella enteritidis*; 21: *Salmonella pullorum*; 22: *Salmonella typhimurium*; 23: *Vibrio parahaemolyticus*; 24: *Escherichia coli*; 25: *Staphylococcus aureus*; 26: *Campylobacter jejuni*; 27: *Campylobacter coli*.

It can be seen that the 2 strains of serotype 4h of *Listeria monocytogenes* both amplified specific bands of 429 bp and 211 bp; 12 strains of other serotypes of *Listeria monocytogenes* all only amplified specific bands of 221 bp; while none of the 13 negative strains had specific amplified bands. The above results indicate that the multiplex PCR method of the present invention is easy to operate and determine result, and has good specificity.

6) Experiment for Evaluating Sensitivity of the Multiplex PCR Method

The genomic DNA of *Listeria monocytogenes* serotype 4h strain XYSN was extracted and the initial concentration was measured. The concentration was adjusted to 100 ng/μL with ddH2O, and then a 10-fold serial gradient dilution was performed to 1 fg/μL and placed on ice for later use. 12.5 μL of 2×Taq Master mix, 1 μL of genomic DNA with various dilutions as template, 10 μM primers lmo1210F, lmo1210R, xysn_1693 F and xysn_1693R (each of which was 1 μL) were added to the PCR tube, respectively, the mixture was filled up to 25 μL with ddH2O and mixed well, and a negative control was established at the same time. After the multiplex PCR reaction was completed, agarose gel electrophoresis was performed to analyze the results.

Figure 2:
FIG. 2 is an experimental result for evaluating sensitivity of the multiplex PCR method in Embodiment 1 of the present invention. Among them, M: DL2000; CK: Negative control; 1-9: Genomic DNA concentrations of Listeria monocytogenes serotype 4h strain XYSN are 100 ng/μL, 10 ng/μL, 1 ng/μL, 100 pg/μL, 10 pg/μL, 1 pg/μL, 100 fg/μL, 10 fg/μL and 1 fg/μL, respectively.

The results are shown in FIG. 2, where M: DL2000; CK: Negative control; 1-9: Genomic DNA concentrations of *Listeria monocytogenes* serotype 4h strain XYSN were 100 ng/μL, 10 ng/μL, 1 ng/μL, 100 pg/μL, 10 pg/μL, 1 pg/μL, 100 fg/μL, 10 fg/μL and 1 fg/μL, respectively. It can be seen that the multiplex PCR method has a detection sensitivity of 100 fg/μL for the genomic DNA of *Listeria monocytogenes* serotype 4h strain, indicating a high sensitivity for this method.

Embodiment 2: Preparation of Kit

The gene lmo1210 detection primer and the gene xysn_1693 detection primer were synthesized, respectively, see Table 1 for details.

The abovementioned primers may be individually packaged or separately packaged, and the amount of the primer may be a conventional amount known to those skilled in the art.

That is to say, the kit of the present invention may contain each set of primer pairs individually packaged as described above, or may contain a prepared PCR detection mixture containing each set of primers.

Further, the above kit may also include other reagents required for PCR, for example, one or more of PCR reaction reagents such as ddH2O, dNTP, PCR buffer, rTaq enzyme and sample genomic DNA extraction reagent.

Embodiment 3: Multiplex PCR Identification of *Listeria monocytogenes* in Samples from Different Sources 35 strains of *Listeria monocytogenes* isolated from retail pork (including chilled fresh meat, cooked meat products), sheep farms, sewage and other samples in the early stage were identified using the multiplex PCR method established in the present invention. The serotypes of these 35 bacterial strains were identified by the slide agglutination experiment. The strain number and serotype are shown in Table 3.

TABLE 3

*Listeria monocytogenes* isolated strain in samples from different sources

| Number | Name | Strain number | Serotype |
|---|---|---|---|
| 1 | Listeria monocytogenes | HA-P161020-D14 | 4h |
| 2 | Listeria monocytogenes | 16E | 4h |
| 3 | Listeria monocytogenes | YZP18063010 | 1/2c |
| 4 | Listeria monocytogenes | YZP18063011 | 1/2c |
| 5 | Listeria monocytogenes | YZP18063012 | 1/2a |
| 6 | Listeria monocytogenes | YZP18063016 | 1/2c |
| 7 | Listeria monocytogenes | YZP1807151 | 1/2c |
| 8 | Listeria monocytogenes | YZP1807152 | 1/2a |
| 9 | Listeria monocytogenes | YZP1807154 | 1/2c |
| 10 | Listeria monocytogenes | YZP1807155 | 1/2a |
| 11 | Listeria monocytogenes | YZP1807158 | 1/2a |
| 12 | Listeria monocytogenes | YZP1807159 | 1/2a |
| 13 | Listeria monocytogenes | YZP18071516 | 1/2c |
| 14 | Listeria monocytogenes | YZ18090703 | 1/2a |
| 15 | Listeria monocytogenes | YZ18090704 | 1/2c |
| 16 | Listeria monocytogenes | YZ18090706 | 1/2c |
| 17 | Listeria monocytogenes | YZ18090709 | 1/2a |
| 18 | Listeria monocytogenes | YZP18091901 | 1/2c |
| 19 | Listeria monocytogenes | YZ18100102 | 1/2a |
| 20 | Listeria monocytogenes | YZ18091403 | 1/2a |
| 21 | Listeria monocytogenes | YZ18091404 | 1/2c |
| 22 | Listeria monocytogenes | YZ18091406 | 1/2c |
| 23 | Listeria monocytogenes | YZ18091409 | 1/2a |
| 24 | Listeria monocytogenes | YZ18120201 | 1/2a |
| 25 | Listeria monocytogenes | YZ18120202 | 1/2c |
| 26 | Listeria monocytogenes | YZ18120203 | 1/2a |
| 27 | Listeria monocytogenes | YZ18120204 | 1/2a |
| 28 | Listeria monocytogenes | YZ18120205 | 1/2c |
| 29 | Listeria monocytogenes | YZ18120207 | 1/2c |
| 30 | Listeria monocytogenes | YZ18120208 | 1/2c |
| 31 | Listeria monocytogenes | YZ18120211 | 1/2a |
| 32 | Listeria monocytogenes | YZ18120213 | 1/2a |
| 33 | Listeria monocytogenes | Lm03061803 | 4c |
| 34 | Listeria monocytogenes | Lm03061102 | 4b |
| 35 | Listeria monocytogenes | NTSN | 4b |

The method for extracting the genomic DNA template of the strain was carried out in accordance with the method by using the conventional bacterial DNA extraction kit. DNA was amplified using the kit prepared in Embodiment 2: 12.5 μL of 2×Taq Master mix, 1 μL of genomic DNA template, 10 μM primers lmo1210F, lmo1210R, xysn_1693 F and xysn_1693R (each of which was 1 μL) were added into PCR tube, respectively, the mixture was filled up to 25 μL with ddH2O and mixed well, and a negative control was established at the same time. After the multiplex PCR reaction was completed, agarose gel electrophoresis was performed to analyze the results.

Figure 3A:
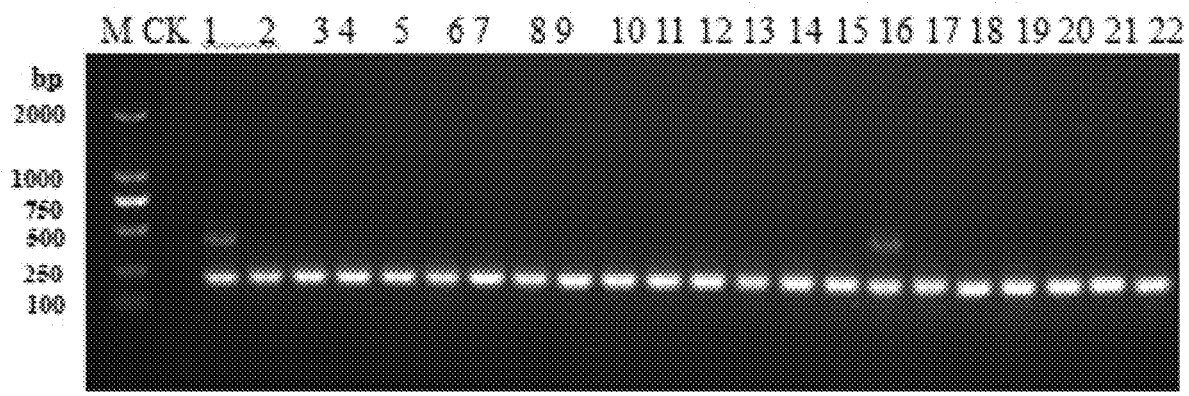
FIG. 3a and FIG. 3b are the results of multiplex PCR detection of Listeria monocytogenes in samples from different sources in Embodiment 2 of the present invention. Among them, M: DL2000; CK: Negative control; 1: Listeria monocytogenes XYSN (serotype 4h); 2: Listeria monocytogenes EGD-e (serotype 1/2a); 3-37: Listeria monocytogenes isolated in samples from different sources.
Figure 3B:
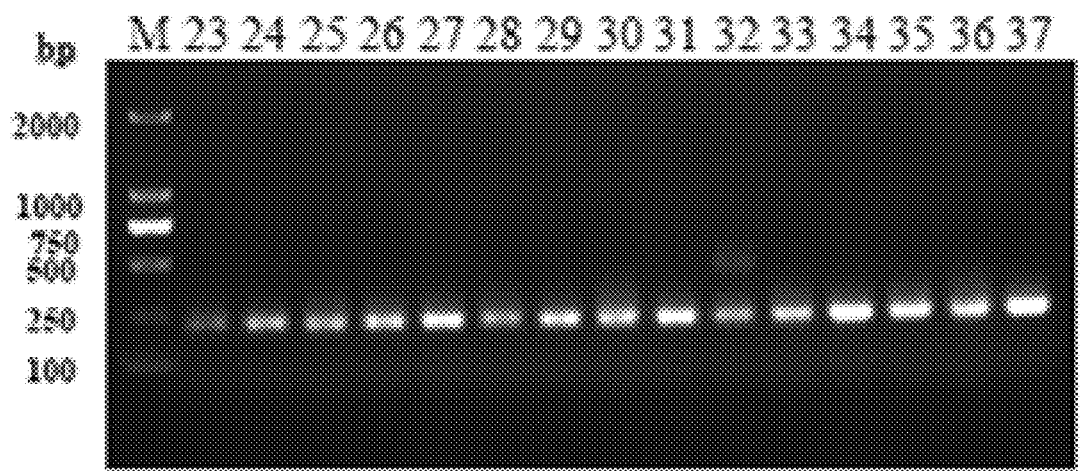

The multiplex PCR identification results are shown in FIG. 3a and FIG. 3b. These 35 bacteria strains are all *Listeria monocytogenes*, which are consistent with the previous identification results of the bacteria, indicating a high accuracy of the multiplex PCR detection method. At the same time, it can be seen from the multiplex PCR method that there are two strains of serotype 4h of *Listeria monocytogenes* among 35 strains, namely 16E and HA-P161020-D14. The commercial diagnostic serum can identify 13 *Listeria monocytogenes* serotypes including 1/2a, 1/2b and 1/2c, except for the recently reported serotype 4h, and the multiplex PCR method is a supplement to it and does not result in misdiagnosis.

Compared with the traditional method, the present invention has the advantage that the sample can be directly subjected to multiplex PCR identification after bacteria enrichment and selective culture, and the result can be determined within 3 h without the need for preliminary screening by sugar fermentation test and subsequent identification by a biochemical experiment, which saves time, has lower cost, simple operation, and is suitable for sample detection.

The above embodiments are intended to describe the implementation disclosed in the present invention, and cannot be construed as limiting the present invention. In addition, various modifications and changes in methods and compositions listed in the present invention are easily understood by a person skilled in the art without departing from the scope and spirit of the present invention. Although the present invention is described in detail by combining with various specific preferred examples of the present invention, it should be understood that the present invention should not be limited to these specific examples. In fact, various modifications described above which are easily understood by a person skilled in the art and used to obtain the present invention should be included in the scope of the present invention.

What is claimed is:

1. A method for detecting *Listeria monocytogenes* serotype 4h, comprising the following steps of:
   (1) extracting a sample genomic DNA;
   (2) adding samples comprising adding the sample genomic DNA into a first PCR tube, adding a positive control into a second PCR tube, and/or adding a negative control into a third PCR tube, wherein each of the PCR tubes is filled provided with a PCR reaction system, wherein the PCR reaction system comprises a gene lmo1210 detection primer pair and a gene xysn_1693 detection primer pair;
   wherein the gene lmo1210 detection primer pair consists of a forward primer having a nucleotide sequence consisting of SEQ ID NO: 3 and a reverse primer having a nucleotide sequence consisting of SEQ ID NO: 4, and the gene xysn_1693 detection primer pair consists of a forward primer having a nucleotide sequence consisting of SEQ ID NO: 6 and a reverse primer having a nucleotide sequence consisting of SEQ ID NO: 7,
   (3) performing PCR reaction, comprising placing the PCR tubes on a PCR instrument, and setting circulation parameters, to carry out the PCR reactions; and
   (4) analyzing results after the PCR reaction is completed, wherein when the sample comprises *Listeria monocytogenes* serotype 4h, a 211 bp band and a 429 bp band are detected simultaneously, wherein when the sample comprises no *Listeria monocytogenes* serotype 4h, a 211 bp band or no band is detected.

2. The method for detecting *Listeria monocytogenes* serotype 4h according to claim 1, wherein conditions for the PCR reactions in step (3) comprises: pre-denaturation at 95° C. for 5 min; 35 cycles of denaturation at 95° C. for 30s, annealing at 55° C. for 30s, and extension at 72° C. for 30s; and termination at 72° C. for 10 min.

3. The method for detecting *Listeria monocytogenes* serotype 4h according to claim 1, wherein the analyzing of results in step (4) further comprises: if only the 211 bp band is amplified, it is determined to be positive for other serotypes of *Listeria monocytogenes*; and if no band is amplified, it is determined to be negative for *Listeria monocytogenes*.

* * * * *